United States Patent [19]
Logé et al.

[11] Patent Number: 5,924,864
[45] Date of Patent: Jul. 20, 1999

[54] HANDPIECE FOR MEDICAL PURPOSES, IN PARTICULAR FOR A MEDICAL OR DENTAL TREATMENT DEVICE, PREFERABLY FOR A CUTTING TREATMENT OF A DENTAL ROOT CANAL

[75] Inventors: Hans Logé, Biberach; Bernhard Kuhn, Schemmerhofen; Bernd Gugel, Ulm-Einsingen, all of Germany

[73] Assignee: Kaltenbach & Voigt GmbH, Biberach, Germany

[21] Appl. No.: 09/047,337

[22] Filed: Mar. 25, 1998

[30] Foreign Application Priority Data

Apr. 18, 1997 [DE] Germany ............... 197 16 416
Oct. 13, 1997 [DE] Germany ............... 197 45 245

[51] Int. Cl.$^6$ .............. A61C 1/07; A61C 3/03; A61C 3/08
[52] U.S. Cl. ............. 433/118; 433/112; 433/131
[58] Field of Search .................... 433/118, 119, 433/112, 114, 104, 105, 126, 131, 136

[56] References Cited

U.S. PATENT DOCUMENTS

| | | | |
|---|---|---|---|
| 1,753,352 | 4/1930 | Stark | 433/112 X |
| 1,875,559 | 9/1932 | Brumm | 433/112 X |
| 3,578,745 | 5/1971 | Garnier | 32/57 |
| 4,338,798 | 7/1982 | Gilman | 464/23 |
| 5,529,495 | 6/1996 | Edwards | 433/112 |

*Primary Examiner*—Nicholas D. Lucchesi
*Attorney, Agent, or Firm*—Fitzpatrick, Cella, Harper & Scinto

[57] ABSTRACT

In the case of a handpiece (3) for medical purposes, preferably for a cutting treatment of a dental root canal, with a tool holder (5) arranged in the front end region of the handpiece (3), with a retaining coupling (16) for detachable fastening of the tool (6) in the tool holder (5) and with a drive connection (8) extending lengthwise through the handpiece (3) for a rotary and/or reciprocating drive of the tool holder (5), an overload coupling (14) that limits the transmittable torque to a maximum torque value is arranged in the drive connection (8).

25 Claims, 4 Drawing Sheets

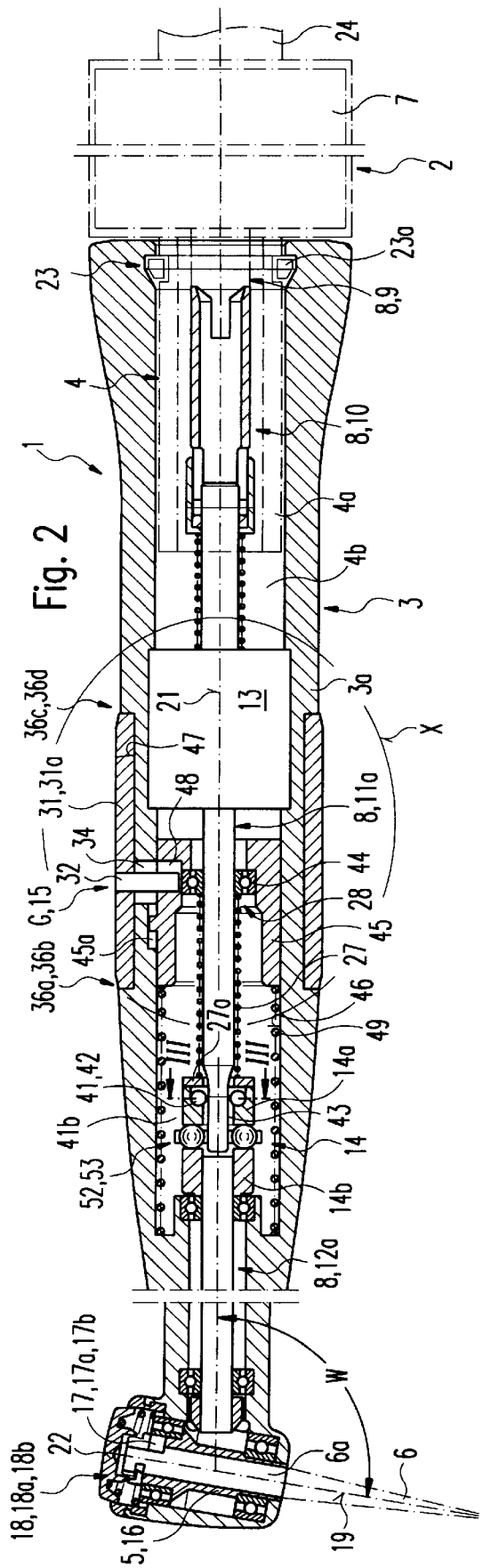

HANDPIECE FOR MEDICAL PURPOSES, IN PARTICULAR FOR A MEDICAL OR DENTAL TREATMENT DEVICE, PREFERABLY FOR A CUTTING TREATMENT OF A DENTAL ROOT CANAL

BACKGROUND OF THE INVENTION

1. Field of the Invention

The invention relates to a handpiece as part of a treatment instrument or processing instrument or as part of a treatment device or processing device for medical purposes.

Such a handpiece may be, inter alia, a medical or dental treatment instrument or a processing instrument for a medical or dental laboratory.

2. Description of the Related Art

Medical or dental handpieces or treatment instruments differ, inter alia, by virtue of the function of the tool borne by them in each instance and by the operation of the drive. A tool may be driven by rotation, as is the case with a drill for example, or by an axial reciprocating movement, as is the case with a file, or also by a combination of these movements. A handpiece with a tool that is driven in rotation may also be used, given appropriate design of the tool, for the purpose of transmitting a rotary drive force to rotating parts, for example for tightening or loosening screws that are present at the treatment site, as is the case, for example, with screws pertaining to false teeth or to other parts of the body.

The use of an existing handpiece is problematic for several reasons. One problem is that, by reason of the rod-shaped design of the handpiece, in the event of a pivoting movement about the axis of the tool it is possible to exert a considerable leverage with it which, with regard to loading, both of the tool and of the tooth, can result in overstressing, for example it can result in the tool snapping or in the tooth being stressed so much as to be levered out. The existing problem arises in particular when the tool is one that serves to prepare a cavity in which the tool can snap, above all when the cross-sectional size of the tool is relatively small, as is the case with a treatment and processing tool for preparing a root canal of a tooth. If such a tool breaks in the course of the treatment it becomes lodged relatively firmly in the cavity accommodating it and in most cases cannot be removed. Possibilities to be reckoned with are that a snapped root-canal tool will impair the function of the tooth and the useful life thereof or may trigger a focus of inflammation resulting in premature loss of the tooth.

The problems described above arise in particular in the case of a handpiece with a root-canal tool because such a tool easily breaks by reason of its relatively small cross-sectional size and length and a fragment gets jammed in the root canal and, in most cases, cannot be extracted.

With such a handpiece, in which the tool performs a rotary-drive function, problems resulting from an overload may likewise arise, for example when a screw thread that serves to attach a tooth or a part of the body is overwound.

SUMMARY OF THE INVENTION

The object underlying the invention is to configure a handpiece of the existing type in such a way that, in particular, overloads of the tool or of the object to be treated that result from the drive are avoided.

According to one aspect of the invention there is provided in a handpiece for a medical or dental treatment device, a tool holder arranged in a front end region of the handpiece; a retaining coupling constructed and arranged to permit detachable fastening of a tool in the tool holder; a drive connection extending lengthwise through the handpiece for driving the tool holder; and an overload coupling arranged in the drive connection in a manner which limits transmittable torque to a maximum torque value. The overload coupling comprises a driving element for connection to a source of driving force, a driven element connected to the tool holder, a coupling for transmitting drive force from the driving element to the driven element and an adjusting means for adjusting the maximum amount of drive force transmittable by the coupling.

In the configuration according to the invention an overload coupling that is adjusted to a maximum torque-transmission value and is therefore triggered automatically if the predetermined torque is exceeded is integrated into the drive connection of the tool. By this means an overload of the tool itself or of a part of the body or a replacement body part that is subject to the action of the tool is avoided.

The overload coupling according to the invention may be provided at various places on the drive connection. For example, it is possible to integrate the overload coupling into the drive-shaft section or into the retaining coupling for the tool. The essential point is that the overload coupling functions as the weakest link of the drive connection and performs the safety function that is being striven for.

The place where the overload coupling is arranged can be significant, particularly in the case of a handpiece for a dental treatment device, since the arrangement of the overload coupling unavoidably results in a partially larger structural design, and at the working-site of such a handpiece, namely in the oral cavity of the patient, on the one hand little space is available and on the other hand an enlargement of the structural design impedes the view of the treatment point that is necessary for careful observation in the course of the treatment.

With the overload coupling according to the invention, rotary drive below the predetermined torque value is guaranteed. Such a coupling is suitable in highly advantageous manner, particularly a sliding coupling which slips at a level above the aforementioned torque value and, in the event of a diminution of the torque to be transmitted, reassumes the coupling function automatically. This purpose is fulfilled in highly advantageous manner by two flat rubbing surfaces arranged at right angles to the existing axis of rotation or by two rubbing surfaces that are rotationally symmetrical with respect to the coupling axis on two coupling discs, one or both of which is/are supported so as to be axially displaceable and which is/are biased with respect to one another by spring tension.

Within the scope of the invention it is also advantageous to design the coupling surfaces of the coupling parts facing one another with wedge-shaped elevations and depressions matching one another and having similar, relatively large flank angles of about 135° and more, whereby the extent of the axial displacement of one or both discs corresponds at least to the axial extent of the elevations in order to guarantee triggering of the overload coupling.

Within the scope of the invention it is at the same time possible and advantageous if roller bodies, in particular balls, are arranged between the rubbing surfaces of the coupling parts in the manner of a crown. Moreover it is also possible to form the wedge-shaped elevations and depressions by means of spherical indentations, the cross-sectional shape of which is preferably adapted to the cross-sectional shape of the roller bodies.

In the case of a configuration with the aforementioned dentiform surfaces of action an effective transfer moment arises and, in the event of slipping, also vibrations and small impacts, effective in the circumferential direction, which further improve the effectiveness and, depending on the direction of rotation, can bring about release of a trapped tool or of a part subject to the action thereof, such as a screw.

It is furthermore advantageous, particularly for a dental handpiece, to arrange the overload coupling in the rear region of the handpiece in which a partial enlargement of the structural design caused by the overload coupling is less or barely inconvenient, and wherein a small structural design can be realised in the region of the head of the handpiece. In the case of an angular dental handpiece it is advisable to arrange the overload coupling in the rear arm of the angularity.

In order to attain a low operating speed either for a root-canal treatment or for a different treatment or form of processing it is advantageous to integrate a reducing gear into the drive connection of the handpiece and consequently also into the handpiece.

The configuration according to the invention is highly suitable for a handpiece that is capable of being connected to, and released again from, a so-called connecting piece in a manner that is easy to manage by means of a quick-closing connection such as a plug-in connection, said connecting piece being connected by means of a so-called supply hose to a control device pertaining to a treatment unit, for example to a treatment chair.

Particularly in the case where the handpiece according to the invention is designed as a structural unit with the overload coupling and a reducing gear it is possible to utilise a connecting piece that is designed for many types of treatment or processing also by way of drive component for a handpiece according to the invention. Consequently, for a plurality of different treatment or processing operations only one common connecting piece is required, onto which different handpieces and also the handpiece according to the invention are capable of being mounted at will.

With all the configurations described above and particularly in the case of a handpiece with a root-canal tool it is advantageous to configure the overload coupling in such a way that the torque value at which it opens or closes is capable of being adjusted in magnitude. In this regard it is advantageous to provide an adjusting element that is manually accessible from outside and capable of being moved into at least two positions and in the process brings about an infinitely variable adjustment, or an adjustment in steps, of different torque values. Suitable in highly advantageous manner by way of adjusting element is a thin ring that for ergonomic reasons does not impair the handling of the handpiece.

The treatment of the human or animal body or of medical models or artificial body parts in many cases requires treatment or processing in ergonomically difficult positions, as is the case, for example, in the course of the treatment of a tooth in the region of the upper jaw or also in the rear region of the oral cavity. In addition, precision operations need to be carried out with the aid of a handpiece, as is the case, for example, with a root-canal treatment in which particularly careful handling is required, both for reasons of precision and for reasons associated with the risk of breakage. For the purpose of supplying them with drive power and also with particular treatment media, conventional handpieces are connected to a supply device by means of a so-called flexible supply hose. Although the supply hose is flexible, it results in a certain impairment of the handling of the handpiece.

The further object underlying the invention is therefore to improve the handling in the case of a handpiece that, in particular, is equipped for a root-canal treatment.

According to another aspect of the invention, there is provided in a handpiece for a medical or dental treatment device, the combination of a tool holder arranged in a front end region of the handpiece; a retaining coupling constructed and arranged to permit for detachable fastening of a tool in the tool holder; and a drive connection arranged in the handpiece in a forward direction to permit at least one of a rotary and a reciprocating drive of the tool holder. The handpiece is constructed to accommodate, in a rear end region thereof, a receiving device for a battery, an electronic control device and an electrical drive motor. At least one of an electronic control device and an overload coupling is arranged in the drive connection to limit transmittable torque through the drive connection to a maximum torque value; and an adjustment means is provided for adjusting the maximum amount of the transmittable torque.

With this configuration according to the invention the handpiece is independent of a supply hose and for this reason an impairment of the movement of the handpiece such as may be predetermined by a supply hose no longer arises. A further advantage of this configuration according to the invention also consists in that, by reason of its independence of a supply device of the conventional structural design, the handpiece can be carried along as a so-called pocket instrument and can also be applied at locations where a conventional supply device is not available.

BRIEF DESCRIPTION OF THE DRAWINGS

The invention and further advantages that can be achieved with it are described below in greater detail on the basis of drawings and advantageous configurations. Illustrated are:

FIG. 2 a handpiece according to the invention in modified configuration in longitudinal section;

FIG. 3 a partial section III—III in FIG. 2 on an enlarged scale;

FIG. 4 a component of the treatment instrument from FIG. 2 in top view;

FIGS. 5 to 8 modified configurations of the handpiece according to the invention as shown in FIG. 2, on an enlarged scale;

DETAILED DESCRIPTION OF THE PREFERRED EMBODIMENTS

Figure 1:
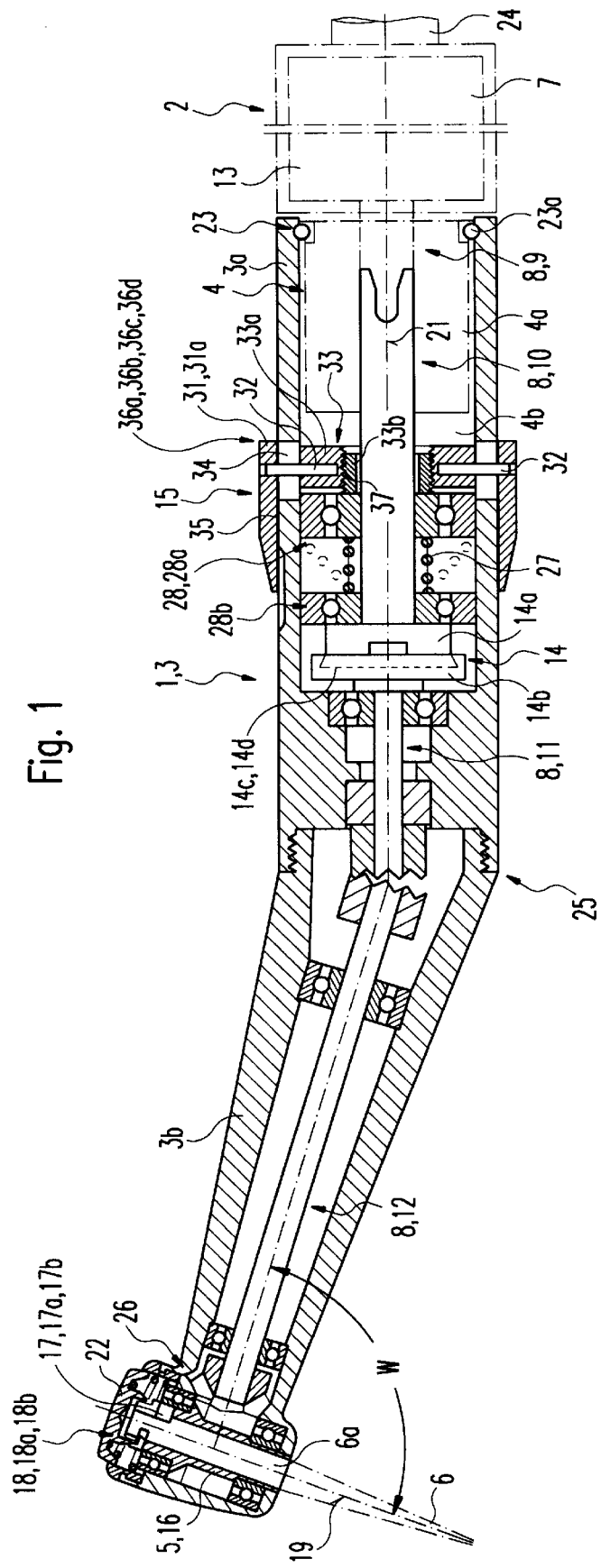
FIG. 1 a dental treatment instrument according to the invention with a handpiece in longitudinal section.

The main parts of the treatment instrument generally designated by 1 are a connecting piece 2 forming the rear end of the treatment instrument, the handpiece 3 which is detachably connected to the connecting piece 2 by means of a quick coupling 4 in the form of a plug-in coupling and which in the coupled-together state extends forward in the manner of a rod from the connecting piece 2 in the form of a gripping sleeve, a tool holder 5 arranged at the front end of the handpiece 3 for a treatment tool or processing tool 6, in particular for a root-canal tool, a preferably electrical drive motor 7 in the connecting piece 2, a drive-shaft train generally designated by 8 which extends lengthwise through the handpiece 3 that forms a gripping sleeve and which consists of several drive-shaft sections 9, 10, 11, 12 that are each connected, or capable of being connected, to one another by means of a coupling, a reduction gear 13 assigned to the drive-shaft train 8 in the region of the connecting piece 2 or of the handpiece 3, an overload coupling 14 assigned to the drive-shaft train 8 in the region of the connecting piece 2 or of the handpiece 3 which is triggered automatically when a certain torque value is attained, and an adjusting device 15 with which this torque value is capable of being changed and with which consequently the overload coupling 14 is capable of being adjusted.

In the configuration represented in FIG. 1 the handpiece 3 extends in angular manner at an obtuse angle with a rear handpiece section 3a and a front handpiece section 3b. However, according to another embodiment example that is yet to be described the handpiece 3 may also extend in straight manner.

In the present embodiment example the tool holder 5 is formed by a receiving sleeve 16 into which the tool 6 with its tool shank 6a is capable of being inserted and is detachably connected to the receiving sleeve 16 by means of a rotary-drive coupling 17 and an axially effective retaining coupling 18. The central axis 19 of the receiving sleeve 16 and also of the tool 6 is directed at right angles to the longitudinal central axis 21 of the handpiece 3 or of the treatment instrument 1, an obtuse angle W of about 90° to about 100° or an angle W of about 90° or 100° being included between these central axes 19, 21 on the side of the tool 6.

The rotary-drive coupling 17 comprises a coupling element 17a which is set into a non-circular coupling recess 17b that is open towards the free end of the tool shank 6a and is formed here by a flattening of the tool shank 6a. The retaining coupling 18 comprises a coupling element 18a that is supported so as to be radially adjustable with respect to the central axis 19 and that by means of a spring force upon insertion of the tool shank 6a into the receiving sleeve 16 is automatically set into a preferably annular coupling recess 18b in the tool shank 6a. For the purpose of releasing the retaining coupling 18, on the side of the thickened end of the handpiece, here taking the form of a head, facing away from the tool 6 an actuating member 22 is arranged which here is preferably supported so as to be coaxially displaceable and which in the event of a movement produced by finger pressure displaces the coupling element 18a into its disengagement position releasing the tool shank 6a. The rotary-drive coupling 17 and the retaining coupling 18 are couplings known as such, so a detailed description may be dispensed with.

The quick coupling 4 is preferably constituted by a plug-in coupling which interlocks in detachable manner in the assembled position. This plug-in coupling is preferably so designed that in the assembled position the drive part 2 and the handpiece 3 are supported so as to be freely rotatable relative to one another about the longitudinal central axis 21. By this means the handling of the handpiece 3 is substantially improved, since the connecting piece 2 does not need to participate in rotary movements of the handpiece 3 during the treatment. The rotary plug-in coupling comprises a hollow cylindrical coupling pin 4a on one coupling part and a coupling recess 4b receiving said coupling part subject to slight movement clearance. With the present configuration the coupling pin 4a extends forward from the connecting piece 2 and the coupling recess 4b is arranged in the rear end region of the handpiece 3. With a view to interlocking in the coupling position, use is made of an interlocking device 23 that is capable of being pushed over having an interlocking element 23a which is arranged in a recess in the external cylindrical surface of the plug-in pin 4a or in the internal cylindrical surface of the plug-in recess 4b and which by means of a spring is set into an interlocking recess located in each instance opposite said interlocking element arranged in the other part in such a way that the interlocking device 23 can be pushed over by an axial tensile force which can be easily applied manually.

The connecting piece 2 is connected by means of a flexible supply hose 24, which is only hinted at in the Figures, to a control instrument, which is not represented, as is conventional for a dental treatment site. Through the supply line 24 there extends a current supply line for the drive motor 7 and, optionally, media lines with lines for air, water and/or spray which extend through the quick coupling 4 in a manner known as such so as to be functional in every rotary position, passing through as far as the front end region of the handpiece 3, where they lead out and are directed towards the treatment point.

The first drive-shaft section 9 extends from the drive motor 7 into the region of the quick coupling 4 where it is connected to the second drive-shaft section 10 by means of plug-in coupling elements engaging one another in positive manner which are coupled simultaneously and automatically when the quick coupling 4 is assembled. The second drive-shaft section 10 extends forward as far as the overload coupling 14 which is located in the central region of the handpiece 3, here of the rear handpiece arm 3a. From the overload coupling 14 the third drive-shaft section 11 extends as far as the apex 25 of the angularity, in the region of which a bevel-gear transmission is arranged, the toothed wheels of which are connected in torsion-resistant manner to the third and fourth drive-shaft sections 11, 12. The fourth drive-shaft section 12 which extends within the front handpiece section 3b is connected by means of a toothed gearing 26 or bevel-gear transmission to the receiving sleeve 16, as a result of which the rotary drive of the latter is guaranteed. It is also possible to provide a transmission here that converts the rotary movement of the drive-shaft section 12 into an axial movement of the receiving sleeve 16, by means of which an axial reciprocating drive for the tool 6 is created. Moreover it is also possible to design the transmission between the drive-shaft section 12 and the receiving sleeve 16 in such a way that it drives the receiving sleeve 16 and consequently also the tool 6 in the sense of an axial reciprocating movement and a rotary movement.

The drive-shaft sections 9 to 12 are each rotatably supported by suitable bearings, preferably by conventional roller bearings or ball bearings.

The overload coupling 14 is constituted by two coupling bushes or discs 14a, 14b, the rear coupling disc 14a of which and the front coupling disc 14b of which comprise, on their front and rear respectively, a coupling surface or rubbing surface 14c, 14d with which they are juxtaposed in a plane of rotation arranged at right angles to the longitudinal central axis 21, whereby one coupling disc, here the rear coupling disc 14a, is supported so as to be axially displaceable and is biased by a spring 27, here a cylindrical or conical helical spring, in relation to the other coupling disc 14b. The spring 27 is supported indirectly or directly on the gripping sleeve of the handpiece 3. The coupling discs 14a, 14b are connected in torsion-resistant manner to the associated drive-shaft sections 10, 11. One of the two coupling discs 14a, 14b comprises a hard rubbing surface 14c, so that only one coupling disc, here the rear coupling disc 14a, is a part subject to wear that is exchanged for a replacement. In this regard it is preferably a question of the coupling disc 14a, which is supported so as to be slightly axially displaceable and is pressurised by the spring 27 into its coupling position.

With the adjusting device 15 the compressive stress with which the coupling discs 14a, 14b are biased with respect to one another can be changed and consequently adjusted so that the overload coupling 14 opens, here slips, at different torque values. With the present configuration the bias of the spring 27 is changed with the adjusting device 15. This is achieved by the abutment 28 of the spring 27 being axially adjustable and capable of being locked in the respective adjustment position. This purpose is served by an adjusting member 31 which is capable of being actuated manually from outside and which with a connecting link 32 passes through the handpiece 3 or the gripping sleeve in the radially inward direction and is connected to a slide 33 arranged in the handpiece 3 which in the event of an axial displacement of the adjusting member 31 in the forward direction likewise pushes the abutment 28 forward and thereby increases the bias of the spring 27. In the event of a displacement of the adjusting member 31 in the rearward direction, the abutment 28 that is supported so as to be axially displaceable in the handpiece 3 follows the slide 33 automatically under the spring tension, as a result of which the bias of the spring 27 is decreased. In this regard the change in the torque value can be effected in infinitely variable manner or in steps. With a view to locking in the respective adjustment position of the slide guide that is present, a clamping or locking element, for example, may be provided. With the present configuration the adjusting member 31 is a rotating ring 31a surrounding the gripping sleeve, which has an internal thread with which it is screwed on an external thread of the gripping sleeve. The connecting link 32 is constituted by a pin or a screw which passes through the gripping sleeve in a recess 34 and is set into the slide 33 which preferably takes the form of a ring and surrounds the rotary-shaft section 10 subject to movement clearance. The recess 34 may follow the slope of the thread 35 or extend in the circumferential direction. The slope of the thread 35 should be such that the length of movement in the circumferential direction is sufficient to change the abutment 28 and the torque value in desired manner.

The spring 27 may be clamped between two roller bearings or ball bearings 28a, 28b which are both supported so as to be axially displaceable in the gripping sleeve and on the drive-shaft section 10 subject to slight movement clearance, whereby the front roller bearing 28b may be rigidly arranged on the drive-shaft section 10 and/or on the coupling disc 14a.

It is advantageous to assign to the adjusting member 31 a scaling with a scale 36a and a counter-scaling or an index 36b on the generated surface of the gripping sleeve and on the adjusting member 31 which, on the one hand, makes possible certain settings of the change in torque value and, on the other hand, permits them to be read off. In the case where the adjusting member 31 is adjustable in the axial direction the scaling is also directed axially. At the rotating ring 31a the scaling is directed in the circumferential direction. By reason of the threaded engagement between the rotating ring 31a and the gripping sleeve the mechanical transmission formed in this way is self-locking, so that an unintentional adjustment of the setting cannot occur.

For the purpose of adaptation to root-canal cross-sections of differing size, root-canal tools 6 of differing cross-sectional sizes are available which, with a view to better differentiation, are tagged with a coloured or other marking, for example a marking symbol, in particular on their shanks, which are preferably of equal size. It is therefore advantageous and serves to enable simpler handling if on the adjusting member 31 or on the gripping sleeve one or more coloured or other markings 36c are provided on the adjustment path which are so arranged that in the event of positional agreement with an index 36d arranged on the other part in question a torque value is set that corresponds to the root-canal tool 6 having the same colour or the same marking. By this means a simplified adjustment of the handpiece 2 to the size or to the type of at least one root-canal tool is ensured. In the event of overloads, when the tool is trapped for example, the overload coupling 14 slips or opens, as a result of which the transmittable torque is limited and the tool 6 is protected against overload, particularly against breakage. The marking 36c and the index 36d may be integrated into the scaling 36a, 36b. It is furthermore advantageous to arrange the at least one marking 36c in such a way that it coincides with a lock-in position or the associated lock-in positions 51a, 51b, 51c, as a result of which the adjustment is further simplified.

The slide 33 preferably consists of an outer ring 33a and an inner ring 33b which are coaxially engaged by means of a thread 37, so that as a result of axial screwing of the inner ring 33b relative to the outer ring 33a a desired zero-point setting and consequently a certain initial torque for the overload coupling 14 is capable of being set and consequently the overload coupling 14 is adjustable. By reason of the thread-type engagement this setting is also self-locking, so that unintentional adjustment is prevented. For the purpose of adjustment the inner ring 33b may comprise application elements, recesses for example, on its reverse side for a matching tool (not represented), with which it can be rotated.

The embodiment example according to FIGS. 2 to 7, wherein similar or comparable parts are provided with the same reference symbols, differs from the embodiment example described above in many respects. The reduction gear 13 may be arranged in the handpiece 3 or in the gripping sleeve, here in its rear or central region, in particular in the region of the second drive-shaft section 10. The overload coupling 14 and the adjusting device 15 are arranged offset forwards in relation to the reduction gear 13. In this configuration a handpiece 3 extending in straight manner is provided, but an angularity may also be provided here. Here too the angle W may, both in the case of a straight shape and in the case of an angularity, amount to about 90° to 100° or about 90° or about 100°. The overload coupling 14 is likewise arranged between two drive-shaft sections which are designated here by 11a and 12a.

With the present configuration the axially fixed or front coupling disc 14b is seated in torsion-resistant manner with a bore on the rear end of the drive-shaft section 12a, forming with its front face directed rearward the associated coupling surface or rubbing surface 14d. The rear coupling disc 14a with its coupling surface or rubbing surface 14c is supported with a bore so as to be axially displaceable on the front end region of the drive-shaft section 11a but is connected to the drive-shaft section 11a in torsion-resistant manner by means of a rotary-drive connection. This purpose may be served by at least one driver lug in the central hole of the coupling disc 14a or at least one driver ball 41 which is set into a longitudinal groove 43 in the drive-shaft section 11 subject to movement clearance which leads out axially at the front end of the drive-shaft section 11. The ball 41 is seated in a recess 42 in the coupling disc 14a that is open in the radially inward direction. Two or more driver lugs or balls 41 and longitudinal grooves 43 may be provided located opposite one another in the manner of a multiple-spline shaft connection. A disc 27a may be arranged between the spring 27, which here is arranged on the drive-shaft section 11a, and the coupling disc 14a.

The abutment 28 is constituted here by a bearing ring, in particular a roller bearing or ball bearing 44, which is supported in a cylindrical slide 45 that is supported so as to be axially displaceable and non-rotatable subject to slight movement clearance in a bore 46 in the gripping sleeve 3a. To this end a keyway connection, for example with a lug 45a on the periphery of the slide 45, may be provided which is set into a longitudinal groove in the inner wall of the gripping sleeve 3a subject to movement clearance. Also in this configuration the adjusting member 31 is constituted by a rotating ring 31a which, however, is of hollow cylindrical design and is rotatably supported with its inner circumference on a cylindrical bearing section 47 of the gripping sleeve 3a. In contrast with the embodiment example described above, the transmission G which converts a rotary movement into an axial movement is constituted here by an adjusting groove 48 in the slide 45 that extends obliquely or in curved manner, whereby the connecting link 32, which is, for example, likewise constituted by a pin or a screw and attached to the rotating ring 31a, passes through a hole 34 in the gripping sleeve 3a of correspondingly large dimension enabling the requisite movement and is set into the adjusting groove 48 subject to movement clearance. Here the slide 45 and the roller bearing 44 form a motive unit, whereby the latter is supported so as to be displaceable on the drive-shaft section 11a subject to slight movement clearance and the outer ring of the roller bearing is able to abut a rear shoulder surface in the slide 45. On the reverse side the spring 27 is supported on the slide 45 indirectly via the roller bearing 44. Furthermore a spring 49 may be provided which is preferably constituted by a compression/helical spring that is supported on the front end of the bore 46 in the gripping sleeve and biases the slide 45 in the rearward direction.

Upon manual rotation of the rotating ring 31a the slide 45 or the abutment 28 is adjusted axially by reason of the oblique or curved contour of the adjusting groove 48 which constitutes a guide for the connecting link 32, and consequently the bias of the spring 27 and the torque value are correspondingly changed and set, namely increased or reduced.

In the case of a contour of the adjusting groove 48 without self-locking and/or when certain adjustment steps are to be palpable on the adjustment path by means of pressure points, within the adjusting groove 48 there are assigned lock-in recesses 51a, 51b, 51c, into which the pin-shaped connecting link 32 locks into place under the bias of the spring 49, as a result of which the setting is established in a manner capable of being pushed over manually or as a result of which the adjustment steps are manually palpable. By this means a locking device F that is detachable or capable of being pushed over is formed for the adjusting device 15. FIG. 4 shows the adjusting groove 48 in the developed view. Just like the marking 36c, 36d, the lock-in points 51a, 51b, 51c may also be arranged in positions on the adjustment path that correspond to certain torque values, in particular to the associated different tools 6. The markings 36c are preferably assigned to the lock-in points 51a, 51b, 51c.

In the configuration according to FIG. 2 a scaling with a scale 36a and an index 36 may also be provided on the periphery of the gripping sleeve and of the rotating ring 31a. The lock-in recesses 51a, 51b, 51c may also be provided on the left-hand edge of the adjusting groove 48 if the spring 49 is effective in the forward direction. An oblique or curved adjusting groove 48 may also be provided on the rotating ring 31 for the connecting link 32 if the latter is attached to the slide 45.

According to FIG. 5 or 6 the rubbing surfaces 14c, 14d of the coupling discs 14a, 14b abut one another, the rubbing surfaces 14c, 14d according to FIG. 5 being arranged in a transverse plane directed at right angles to the longitudinal central axis 21. According to FIG. 6 the rubbing surfaces 14c, 14d are formed with axial elevations 14e and depressions 14f matching one another, the flank surfaces of which extend radially and include similar obtuse angles W1 of about 135° to 170°. The shape of the elevations 14e and depressions 14f or of their flanks does not need to take the form of a wedge. A trapezoidal shape or a rounded or curved shape may also be provided.

In the configuration according to FIG. 7 roller elements 52, in particular balls, which are retained in a cage 53 are arranged between the rubbing surfaces 14c, 14d. In the embodiment example according to FIG. 8 spherical indentations 54 are arranged in both rubbing surfaces 14c, 14d, located opposite one another, the shape and size of the spherical indentations preferably corresponding to the shape and size of the roller elements 52, here of the balls.

Whereas in the configuration the capacity of the coupling disc 14a for axial displacement may be slight, in the configurations according to FIGS. 6 to 8 the extent of the axial displacement has to be the same as or greater than the axial depth of the depressions 14f (FIG. 6) or greater than the sum of a pair of depressions 14f according to FIGS. 7 and 8. In the configuration according to FIG. 5 a non-positive transmission of torque takes place. On the other hand, in the configurations according to FIGS. 6 to 8 a forced positive transmission of torque takes place, or a combination of non-positive and positive transmission of torque.

Figure 9:
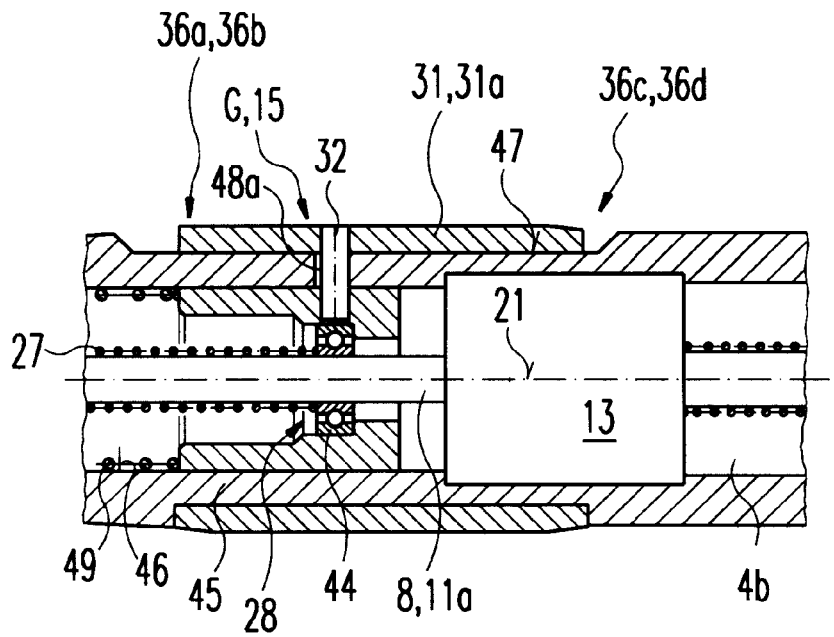
FIG. 9 the detail identified by X in FIG. 2, in modified configuration.
Figure 10:
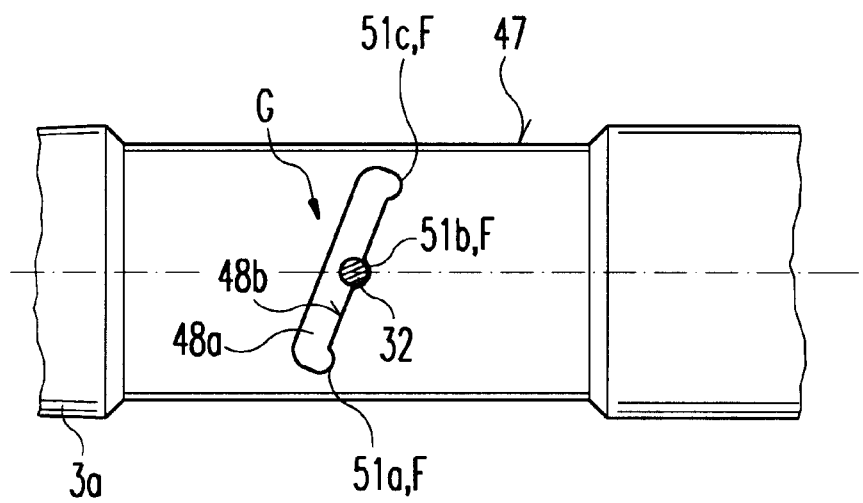
FIG. 10 a part of the configuration according to FIG. 9 in top view.

In the embodiment example according to FIGS. 9 and 10, wherein similar or comparable parts are provided with the same reference symbols, the adjusting groove 48a constituting the transmission G is arranged within the gripping sleeve 3a. In contrast with the embodiment example according to FIG. 4 with a frontal, oblique or curved adjusting surface 48b, the adjusting groove 48a comprises a reverse-side, oblique or curved adjusting groove 48b, along which the connecting link 32 glides in the event of a rotation of the adjusting member 31, whereby the adjusting member 31 and the slide 45, depending on the direction of rotation of the adjusting member 31, are adjustable or adjusted towards the front or towards the rear. The adjusting groove 48 or 48a may be adapted in its axial dimension subject to movement clearance to the axial cross-sectional dimension of the connecting link 32 and may consequently comprise guide surfaces on both sides in the manner of a guide gate that is effective on both sides, or it may also be constituted by a hole that is larger in the axial direction than the connecting link 32, whereby the spring 27 produces the restoring movement in the rearward direction. In the configuration according to FIGS. 9 and 10 the lock-in recesses 51a to, for example, 51c may also be provided in the adjusting surface 48b in order to form lock-in points that are capable of being pushed over. In order to connect the connecting link 32 to the slide 45, a rigid connection may be provided, for example the pin may be firmly pressed into, or adhesion-bonded within, a hole in the slide 45 or the connecting link 32 may also abut the reverse side of the slide 45. A rotationpreventing device for the slide 45 (see reference symbol 45a) is not required.

Figure 11:
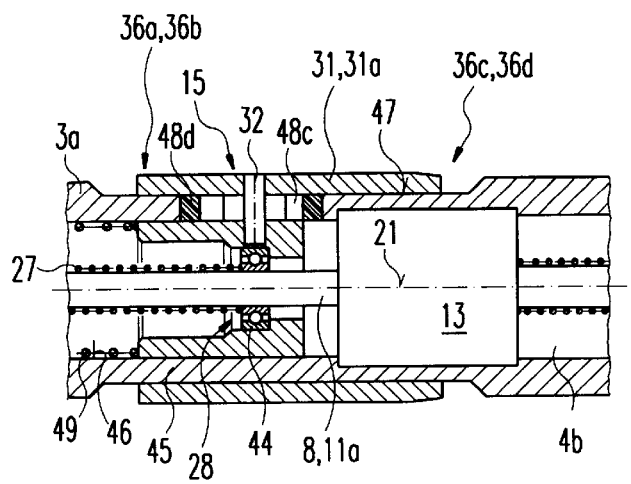
FIG. 11 a detail according to FIG. 9 in further modified configuration.
Figure 12:
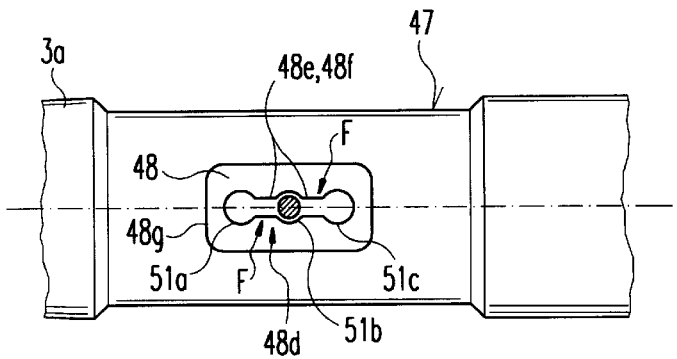
FIG. 12 a part of the configuration according to FIG. 11 in top view.

The embodiment example according to FIGS. 11 and 12, in which similar or comparable parts are likewise provided with the same reference symbols, differs from the embodiment example according to FIGS. 9 and 10 in that the adjusting groove 48c is arranged axially in the gripping sleeve 3a and a locking device F for locking the adjusting member 31 in infinitely variable manner or in steps is provided. A locking device F that is effective in steps may be constituted by clamping or interlocking points in the adjusting groove 48c which preferably forms a guide gate with guide surfaces 48e on both sides. The lock-in points may be formed by lateral recesses. With the present configuration the adjusting groove 48c comprises on one side or on both sides lock-in recesses 51a to, for example, 51c, tapered points 48f being arranged in between them through which the connecting link 32 is capable of being pushed with a certain axial manual expenditure of force and consequently the interlocking is capable of being pushed over. In this regard the connecting link 32 and/or the edge of the adjusting groove 48c may consist of elastically deformable material, preferably rubber or plastic. In this configuration the transmission G is no longer necessary. It is also possible to form the adjusting groove 48a or 48c in an inserted piece 48d made, for example, of rubber or plastic which is seated in a recess 48g of corresponding shape and size in the gripping sleeve 3a.

In the configuration according to FIGS. 9 and 10 the adjusting member executes movements in the circumferential direction and in the axial direction, whereas in the configuration according to FIGS. 11 and 12 it executes movements only in the axial direction or, when the lock-in recesses 51a to 51c have a greater lateral depth, also executes movements in the circumferential direction. The bearing section 47 should be constructed so as to be correspondingly longer than the adjusting member 31.

Figure 13:
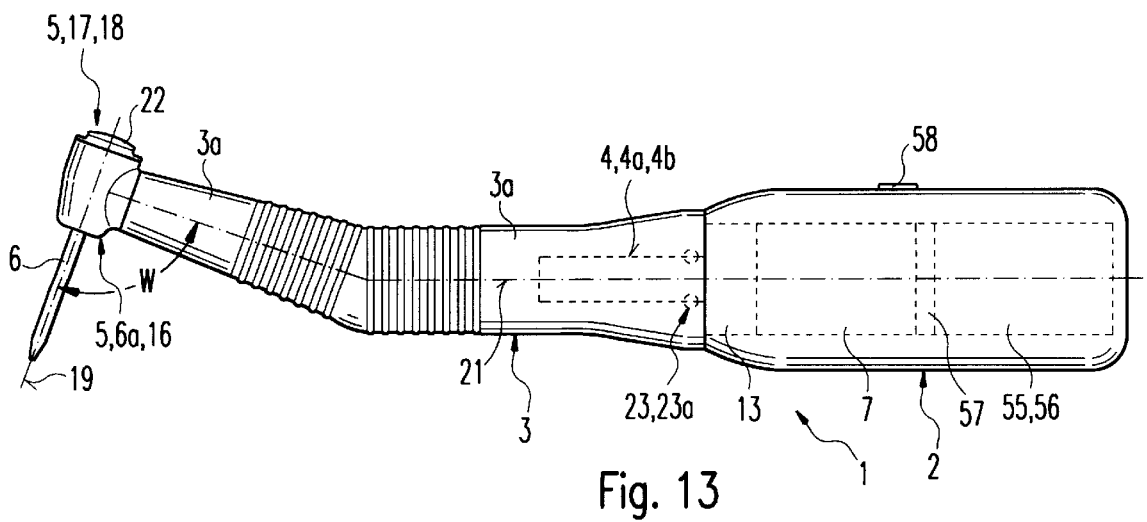
FIG. 13 a handpiece according to the invention in modified configuration in side view.

In the embodiment example according to FIG. 13, wherein similar or comparable parts are provided with the same reference symbols, the treatment instrument 1 is designed as an autarkic instrument with a receiving device 55 for a battery 56 for the current supply of the drive motor 7. The receiving device 55 and the battery 56, as well as an associated electronic control device 57, may be arranged in the connecting piece 2, for example behind the drive motor 7. The handpiece 3 and the quick coupling 4 may be designed so as to correspond to the embodiment example described above. By this means it is possible to subject the handpiece 3 to disinfection or sterilisation, optionally with the requisite heat, and to disinfect the connecting piece 2 or to attend to it in another way. It is also possible to connect the handpiece 3 to the connecting piece 2 in permanently operational manner without a quick coupling. Consequently this treatment instrument 1 may also form a handpiece 3, in the rear end region of which the receiving device 55, the battery 56 and the electronic control device 57 are arranged. The arrangement is preferably designed for a rechargeable battery 56 with a contact arrangement for recharging that is accessible from outside.

In all the embodiment examples described above it is possible to provide, instead of a mechanical torque limiter, an electrical torque limiter which, for example, controls the drive motor 7 in accordance with the current intensity in such a way that a certain maximum torque is not exceeded. In addition, an electrical adjusting device may be provided for changing this torque value. To this end an adjustable adjusting member 58 may be provided, for example on the periphery of the connecting piece 2, on which the variable torque is capable of being adjusted manually.

In all the embodiment examples described above according to FIGS. 1 and 2 an electrical control device for limiting the transmittable torque value or also for adjusting this value may be integrated into, for example, the control instrument which is not represented.

We claim:

1. In a handpiece for a medical or dental treatment device, the combination of:
   a tool holder arranged in a front end region of the handpiece;
   a retaining coupling constructed and arranged to permit detachable fastening of a tool the tool holder;
   a drive connection extending lengthwise through the handpiece for driving the tool holder; and
   an overload coupling arranged in a gripping sleeve region of the handpiece and along the drive connection in a manner which limits transmittable driving force to a maximum driving force.

2. The handpiece set forth in claim 1, wherein:
the overload coupling is arranged in a section of the drive-connection section which extends towards the tool holder.

3. The handpiece as set forth in claim 1, wherein:
said overload coupling comprises two rotatably supported coupling parts arranged coaxially in relation to one another, each of said coupling parts including a rotationally symmetrical rubbing surface, said coupling parts being juxtaposed at their respective rubbing surfaces with said rubbing surfaces being spring-biased against each other.

4. The handpiece as set forth in claim 3, wherein:
said rubbing surfaces extend in a plane which is perpendicular to a longitudinal central axis of the coupling parts.

5. The handpiece as set forth in claim 1, wherein:
one of said coupling parts is supported so as to be axially displaceable and is biased into a coupling position by means of a spring force.

6. The handpiece as set forth in claim 1, wherein:
the overload coupling comprises two rotatably supported coupling parts which are arranged coaxially in relation to one another and which comprise, on sides thereof which face one another in a circumferential direction, a succession of alternate matching depressions and elevations said depressions and elevations having flanks which are axially oblique or rounded, at least one of said coupling parts being supported in elastically yielding manner for the purpose of disengagement.

7. The handpiece as set forth in claim 6, wherein:
said flanks have an included angle which is obtuse and which is substantially in the range of about 135 to 170°.

8. The handpiece as set forth in claim 1 wherein:
said overload coupling comprises two rotatably supported coupling parts which are arranged coaxially in relation to one another and which comprise, on their sides facing one another in a circumferential direction, lines of mutually opposed depressions with axially oblique or rounded flanks, at least one of said coupling parts being supported in an elastically yielding manner for the purpose of disengagement and whereby, between the coupling parts, roller bodies are supported, the cross-sectional size of each of said roller bodies being greater than the sum of the depths of the depressions adjacent such roller body.

9. The handpiece as set forth in claim 8, wherein:
said depressions are formed by spherical indentations that are adapted to the shape and size of the roller bodies.

10. In a handpiece for a medical or dental treatment device, the combination of:

a toolholder arranged in a front end region of the handpiece;

a retaining coupling constructed and arranged to permit for detachable fastening of a tool in the tool holder; and a drive connection arranged in the handpiece and extending in a forward direction to permit at least one of a rotary and a reciprocating drive of the tool holder, said handpiece being constructed to accommodate, in a rear end region thereof, a receiving device for a battery, an electronic control device and an electrical drive motor at least one of an electronic control device and an overload coupling being arranged in said rear end region to limit transmittable driving force through said drive connection to a maximum driving force value.

11. The handpiece as set forth in claim 1 or 10, wherein: the handpiece is detachably connected by means of a quick coupling to one of a rear connecting piece and said rear end region.

12. The handpiece as set forth in claim 1 or 10, wherein: the overload coupling is arranged in one of the central region and the rear region of the handpiece.

13. The handpiece as set forth in claim 1 or 10, further including:

a speed-reducing transmission arranged in one of the central region of the handpiece, the rear end region of the handpiece and the connecting piece.

14. The handpiece as set forth in claim 13, wherein: the overload coupling is arranged at a position upstream of the transmission.

15. The handpiece as set forth in claim 1 or 10, and further including:

an adjusting device for adjusting the torque value in infinitely variable manner or in steps, said adjusting device including an adjusting member that is accessible from outside said handpiece.

16. The handpiece as set forth in claim 15, wherein: the adjusting member is adjustable in a circumferential or axial direction and is arranged on the periphery of the handpiece.

17. The handpiece as set forth in claim 15, and further including:

a locking device arranged in association with one of said adjusting device and said adjusting member to provide detachable locking from a set position.

18. The handpiece as set forth in claim 17, wherein: the locking device comprises a lock-in device which is capable of being pushed over manually to a release position.

19. The handpiece as set forth in claim 15, wherein: said adjusting device is arranged to permit adjustment of the spring force.

20. The handpiece as set forth in claim 15, wherein: the adjusting member is formed by one of a slide and a rotating ring which is connected to the adjusting device by means of a radial connecting link.

21. The handpiece as set forth in claim 15, wherein: the adjusting device comprises one of a thread type drive and a cam drive with a drive connection to the rotating ring.

22. The handpiece as set forth in claim 15, wherein thee is provided along the adjustment path of the adjusting member, a scaling or marking with a counter-scaling or counter-marking or an index; and at least one lock-in point being arranged on the adjusting member and on a part adjacent thereto.

23. The handpiece as set forth in claim 22, wherein: the marking exhibits different symbols or colors.

24. The handpiece as set forth in claim 1 or 10, wherein several different tools are provided which differ from one another with regard to at least one of their shape, size and strength.

25. The handpiece as set forth in claim 24, wherein: each tool exhibits a marking on the tool shank, the position of the marking tool and the lock-in points on the adjustment path corresponding to a predetermined torque value of the associated tool.

* * * * *